US00PP11829P2

(12) United States Plant Patent
Lyrene

(10) Patent No.: US PP11,829 P2
(45) Date of Patent: Apr. 3, 2001

(54) BLUEBERRY PLANT NAMED 'SAPPHIRE'

(76) Inventor: Paul M. Lyrene, University of FL, P.O. Box 110690, Gainesville, FL (US) 32611-0690

( * ) Notice: Subject to any disclaimer, the term of this patent is extended or adjusted under 35 U.S.C. 154(b) by 0 days.

(21) Appl. No.: 09/175,102

(22) Filed: Oct. 19, 1998

(51) Int. Cl.[7] ..... A01H 5/00
(52) U.S. Cl. ..... Plt./157
(58) Field of Search ..... Plt./157

(56) References Cited

U.S. PATENT DOCUMENTS

P.P. 10,675 * 11/1998 Lyrene ..... Plt./157

* cited by examiner

*Primary Examiner*—Bruce R. Campell
*Assistant Examiner*—Wendy Baker

(57) ABSTRACT

A new and distinct low-chill tetraploid highbush blueberry (Vacinnium) variety of complex ancestry, based largely on *V. corymbosum* L with some genes from *V. darrowi* Camp. Its novelty consists of the following unique combination of features:

1. Produces a bush that is upright but somewhat spreading.
2. Has a high resistance to cane canker (*Botryosphaeria corticis*), and moderate resistance to stem blight (*Botryosphaeria dothidia*), and to root rot (*Phytophthora cinnamomi*).
3. Flowers and produces abundant new leaves in areas of central and north Florida where the mean temperature of the coldest month is 62 degrees F. or colder.
4. Ripens its fruit 60 days after flowering in central Florida (latitude 27.5N).
5. Ripens 80% of its fruit between April 10 and May 10 in central Florida.
6. Produces fruit that are large, firm, have a good picking scar, with sweet flavor and good texture.
7. Can be propagated asexually by softwood cuttings.

3 Drawing Sheets

ORIGIN OF THE VARIETY

'Sapphire' was selected as a seedling from a cross made in Gainesville in 1980. The parents, which were unnamed, unpatented varieties, were advanced-generation selections from the University of Florida recurrent selection program, in which the large fruit size, high fruit quality, and short flowering-to-ripening interval of northern highbush cultivars from Michigan and New Jersey were being combined with the low chill requirement, summer heat tolerance, and other southern-adaptation features of the native Florida species, *Vaccinium darrowi*. 'Sapphire' was selected as a seedling in a high-density nursery in May 1982 and as a spaced plant in the second-evaluation plots in May 1984 to establish an 8-plant plot at the University of Florida Horticultural Unit in Gainesville. These ramets were planted in the field in January 1986 and have been observed annually since 1987. A small plot of rooted cuttings was also planted in a test plot in Sebring, Fla. in 1989, and 500 additional plants of Sapphire were planted in the field in Sebring in 1991. 'Sapphire' was selected because of superior fruit quality, consistent yielding, and early ripening in Sebring and in Gainesville in multiple-year comparisons with other southern highbush cultivars.

ASEXUAL PROPAGATION OF THE VARIETY

'Sapphire' has been propagated by rooting softwood cuttings under mist on numerous occasions in Gainesville, Fla. (Alachua County). In every case, all resulting plants have displayed the characteristics of the variety.

BRIEF DESCRIPTION OF THE FIGURES OF THE DRAWING

The first drawing illustrates several 7-year-old specimens of the plant 'Sapphire' in side elevation and shows the multiple trunk and branch scaffolding and also depicts the canopy and upright to spreading growth habit near the end of the harvest period in Sebring, Fla.

The second drawing shows in larger scale the flower clusters of 'Sapphire' early in the flowering period, showing the pinkish color of unopened flowers subjected to cold nights in the field and the white color of open flowers. The clustering habit of the flowers is also shown in the figure.

The third drawing depicts typical berries of 'Sapphire' in close view, indicating the shape and color of the fruit, and also the upper and lower surface of the leaves at the time of fruit ripening.

While the coloration shown in the photographic illustrations provided is as close as is reasonably possible to attain in an illustration of this character, the color designations provided in the specification should be considered to be the closest possible representation of the coloration of the instant plant.

DESCRIPTION OF THE VARIETY

The following is a detailed botanical description 'Sapphire', its flowers, fruit and foliage, based on observation of speciemens grown in the field in Gainesville, Fla. Color descriptions, except those given in common terms, use terminology from "The Pantone Book of Color" by Leatrice Eiseman and Lawrence Herbert; Harry N. Abrams, Inc. Publishers, New York.

Bush: Bush size of 7-year-old plants grown on medium-quality blueberry soil, with irrigation, pine-bark mulch, and annual summer pruning.

*Plant height.*—150 cm.

*Canopy diameter.*—110 cm.

*Vigor.*—Medium.

*Growth habit.*—Semi-upright, somewhat spreading.

*Flower bud density* (*number per unit length of stem*).—High.

*Cold hardiness.*—Except for the flower and fruit, some of which have been killed in some years in Gainesville, by freezes in February and March, 'Sapphire' has not suffered freeze damage to the bush in Gainesville. Dormant plants have withstood temperatures of 18 degrees F. without damage.

*Chilling requirement.*—Based on the time and completeness of vegetative and flower bud break in Sebring, 'Sapphire' appears to have a chilling requirement of about 250 hours below 45 F. after the plants have become winter dormant.

*Productivity.*—Large plants on good soil in Sebring have averaged 5 pounds of fruit per plant per year.

*Suckering tendency.*—After 7 years in the field, plants have 6 to 12 major trunks.

*Color of 2-year-old wood.*—"Sponge", Pantone 16-1118.

*Color of trunks 4 years old and older.*—"Taupe gray" Pantone 17-0808.

Twigs:

*Color of previous summer twigs observed January 30.*—"Pink sand" Pantone 15-1318.

*Internode length.*—1.2 cm on strong upright shoots.

Leaves:

*Leaf length excluding petiole.*—45 mm.

*Leaf width.*—27 mm.

*Shape.*—Obovate.

*Margin.*—Entire.

*Color of upper surface.*—"Avocado" Pantone 18-0430.

*Color of lower surface.*—"Sage" Pantone 16-0421.

*Pubescence, upper surface.*—Numerous short, white hairs on midribs and main veins.

*Pubescence, lower surface.*—Essentially glabrous.

*Pubescence, leaf margins.*—Essentially glabrous.

*Synchrony of leafing and flowering.*—New leaves begin to form at the time of or shortly after flowering.

Flowers:

*Length, pedicel attachment point to the corolla tip.*—9.3 mm.

*Diameter of corolla tube at widest point.*—7.8 mm.

*Corolla aperture diameter.*—4.0 mm.

*Corolla color at anthesis.*—Ranges from "Snow white" Pantone 11-0602 if temperatures remain above 50° F. during flowering to increasingly pink, reaching "Morning Glory", Pantone 15-1920, in unopened flowers, if temperatures fall into the 30's or lower 40's during flowering. Cold-induced pink colors fade to white as the flowers open.

*Flower fragrance.*—None. Stamens and pistil typical for highbush blueberry.

*Pollen abundance.*—High.

*Pollen staining with acetocarmine dye.*—Excellent, near 100%. This indicates that high percentage of the pollen grains are starch-filled and potentially viable. Because southern highbush clones are interspecific hybrids, some varieties have reduced male fertility and reduced pollen stainability.

*Flowering period.*—Full bloom averages February 15 in Gainesville.

*Flower cluster.*—Tight.

*Average number of flowers per cluster.*—7.4.

*Self compatibility.*—Partially self-compatible but must be cross-pollinated for full fruit size and number.

Berry:

*Weight.*—Lead berries average 1.7 to 2.2 g.

*Calyx lobes.*—Irregular and not well developed.

*Berry height.*—11 mm.

*Berry width.*—51 mm.

*Diameter of calyx aperture on mature berry.*—6 mm.

*Berry surface color.*—"Lilac gray", Pantone 14-3903.

*Berry surface color with wax removed.*—"Slate Black", Pantone 19-0814.

*Interior berry flesh color.*—"Frozen Dew", Pantone 13-0513, a whitish-green color.

*Color of washed, dried seeds.*—"Aztec", Pantone 18-1130, a dark brown.

*Surface wax.*—Medium persistent.

*Pedicel scar.*—Small and dry.

*Berry firmness.*—High.

*Berry flavor.*—Sweet, sub-acid, pleasant.

*Berry fragrance.*—None.

*Berry texture.*—Good: thin skins, small seeds, inconspicuous sclereids.

*Maturity date.*—First pick averages April 10 in Sebring and April 20 in Gainesville.

Diseases, insects, and mites:

*Cane canker.*—Highly resistant.

*Dieback due to stem blight and root rot.*—Moderately resistant.

*Leaf spots.*—Medium resistant.

*Bud mites.*—Resistant.

Ease of propagation: Roots readily from softwood cuttings.

I claim:

1. A new and distinct highbush blueberry plant, substantially as illustrated and described, characterized by its semi-upright bush, very low chill requirement for both flower and leaf buds, and large, high-quality, early-ripening fruit, having the ability to be asexually propagated by softwood cuttings.

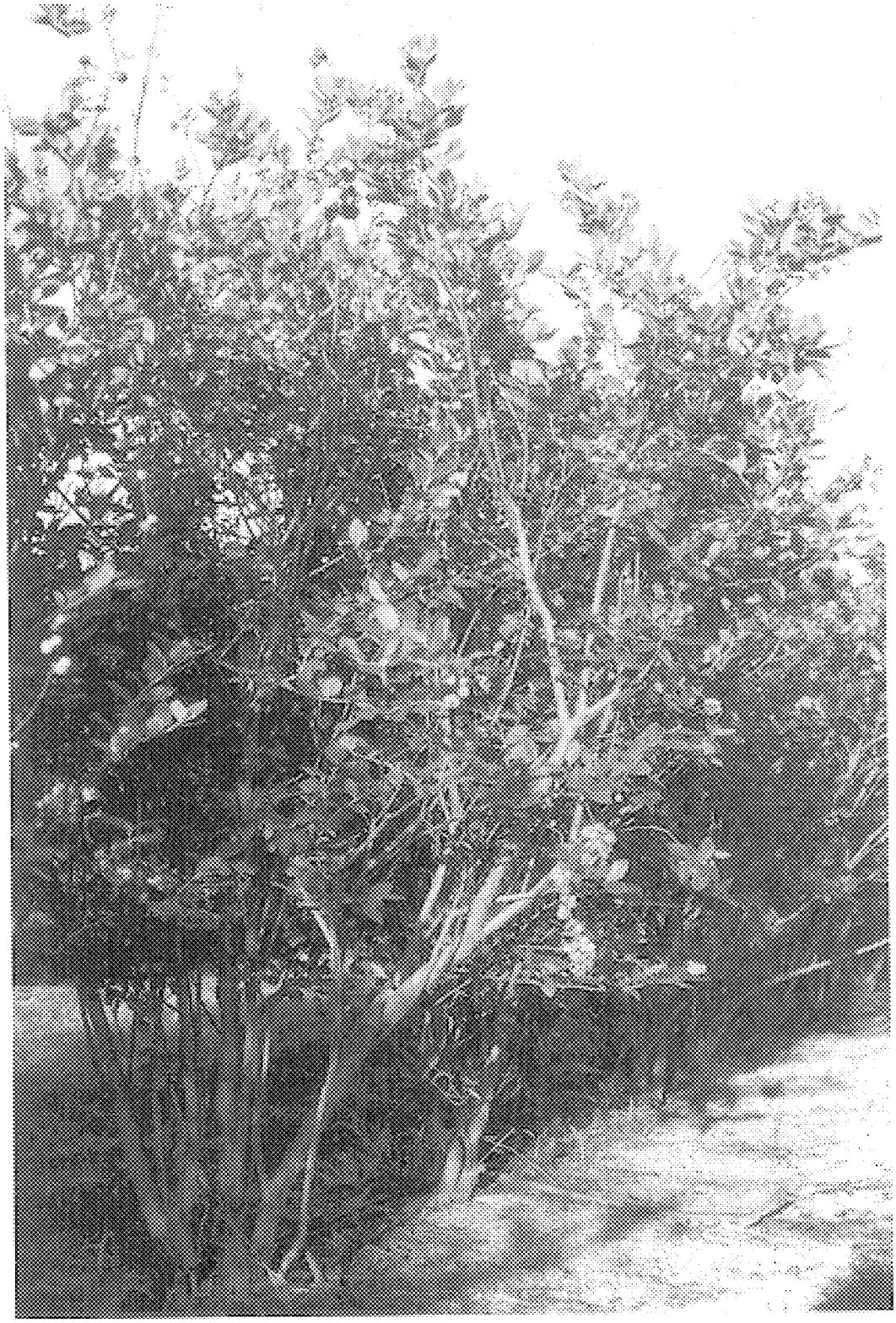

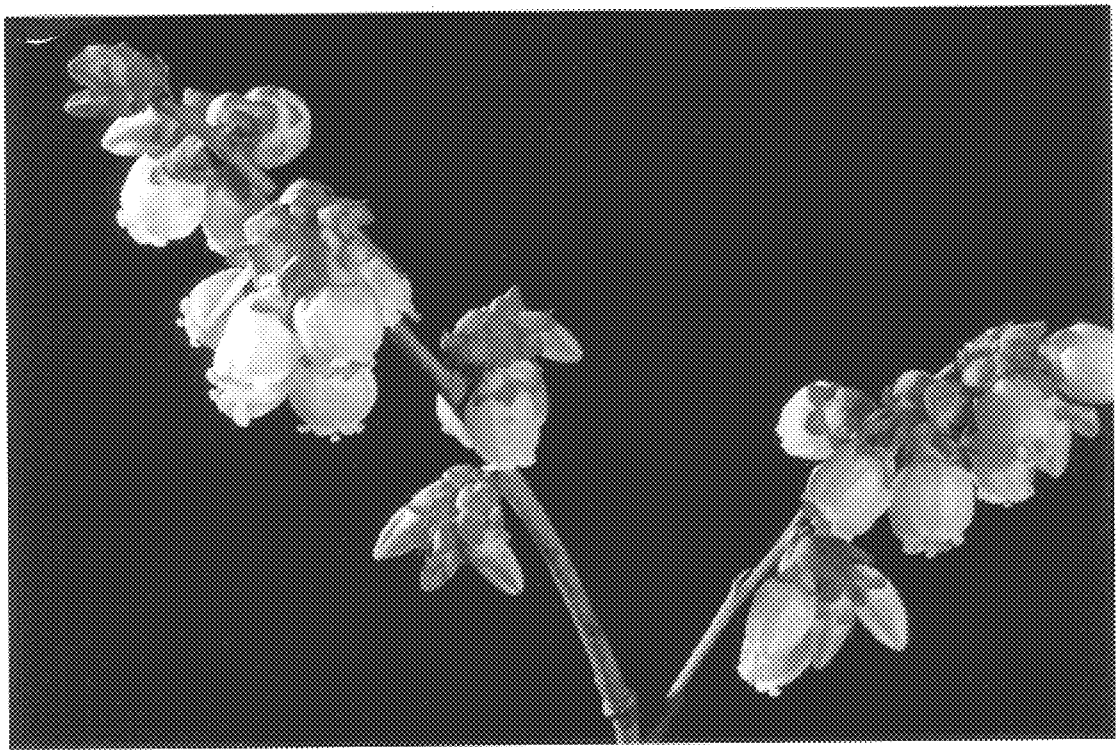

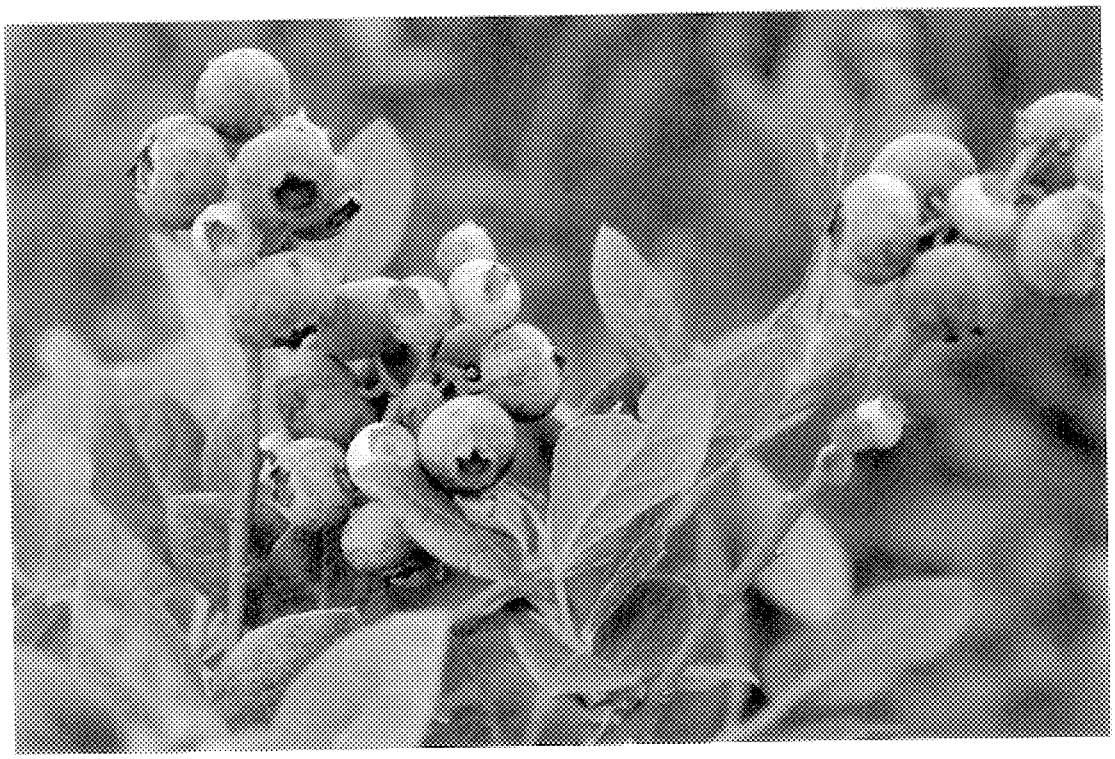

* * * * *